United States Patent [19]

Ellis et al.

[11] 4,172,854

[45] Oct. 30, 1979

[54] DEHYDROGENATION PROCESS AND CATALYST

[75] Inventors: Michael C. Ellis; Harold E. Manning, both of Houston, Tex.

[73] Assignee: Petro-Tex Chemical Corporation, Houston, Tex.

[21] Appl. No.: 539,909

[22] Filed: Jan. 9, 1975

Related U.S. Application Data

[62] Division of Ser. No. 484,576, Jul. 1, 1974, Pat. No. 3,960,776.

[51] Int. Cl.$^2$ .............................................. C07C 15/00
[52] U.S. Cl. .................................. 585/445; 585/630; 585/631; 585/662; 585/663
[58] Field of Search ............ 260/669 R, 680 R, 683.3; 252/468

[56] References Cited

U.S. PATENT DOCUMENTS

| 1,984,884 | 12/1934 | Lazier | 252/468 |
|---|---|---|---|
| 2,205,140 | 6/1940 | Heard | 252/468 |
| 2,205,141 | 6/1940 | Heard | 252/468 |
| 2,209,458 | 7/1940 | Heard et al. | 252/468 |
| 2,474,440 | 6/1949 | Smith et al. | 260/683.3 |
| 2,943,067 | 6/1960 | Sieg | 260/683.3 |
| 3,064,062 | 11/1962 | Lorz et al. | 260/680 R |
| 3,522,323 | 7/1970 | Duke et al. | 260/669 R |
| 3,767,596 | 10/1973 | Manning | 252/468 |
| 3,780,129 | 12/1973 | Friedrich | 260/683.3 |
| 3,781,376 | 12/1973 | Manning | 260/680 R |

*Primary Examiner*—Delbert E. Gantz
*Assistant Examiner*—Joseph A. Boska
*Attorney, Agent, or Firm*—Kenneth H. Johnson

[57] ABSTRACT

Magnesium chromite dehydrogenation catalysts are improved by incorporation therein up to about 10% of an alkali metal.

6 Claims, No Drawings

DEHYDROGENATION PROCESS AND CATALYST

This is a division of application Ser. No. 484,576 filed July 1, 1974, now U.S. Pat. No. 3,960,776.

BACKGROUND OF THE INVENTION

This invention relates to a process for the dehydrogenation of gaseous hydrocarbons and the catalyst employed. More specifically the process is a cyclic process wherein there are alternating cycles of dehydrogenation and catalyst regeneration.

The process is a cyclic process in which gaseous hydrocarbons such as butane, isopentane or ethylbenzene are dehydrogenated over a suitable catalyst to produce butenes and butadiene, isopentene and isoprene and styrene, respectively. After each dehydrogenation cycle there is a catalyst regeneration cycle in which the accumulated coke is burned off by passing molecular oxygen through the catalyst followed by another dehydrogenation cycle and so on.

The chromia-alumina catalysts have been recognized for a number of years as the most preferred catalysts for this type of process. The chromia-alumina catalysts are prepared by treating activated alumina with a solution of chromic acid, draining off the excess acid from the alumina, drying and heat treating at about 1400° F. Commercial chromia-alumina dehydrogenation catalysts normally contain about 20% chromium oxide. Preparative methods are shown, for example, in U.S. Pat. Nos. 2,399,678 and 2,419,997.

Other chromia-metal oxide materials have been investigated for their dehydrogenation capabilities. One of the more prominent among these has been chromia-magnesia which has been found to be a poor second to chromia-alumina. Several patents were issued to Tropsch in the late 1930's relating to magnesia based chromia dehydrogenation catalysts, e.g., U.S. Pat. Nos. 2,122,786; 2,122,787; 2,122,790; and 2,148,140. Pitzer disclosed chromia-magnesia-alumina dehydrogenation catalyst in U.S. Pat. No. 2,638,455. U.S. Pat. No. 3,781,376, discloses magnesium chromites promoted with aluminum.

It is a principal feature of the present invention that improved magnesium chromite catalysts have been developed. It is another feature of the present invention to find a catalyst superior to the chromia-alumina catalysts for use in dehydrogenation. It is still an advantage that a process which will give better results than presently achieved with chromia-alumina catalysts has been provided. Other features and advantages of the present invention will be apparent from the following description.

SUMMARY OF THE INVENTION

It has been found that magnesium chromites are benefited by combination with a small amount, i.e., modifying amount of an alkali metal. Generally, up to about 10 mol percent of the alkali metal based on $MgCr_2O_4$ may be employed. The present invention also relates to the processes of dehydrogenation employing the improved catalysts.

DETAILED DESCRIPTION OF THE INVENTION

The catalysts of this invention contain magnesium, chromium and oxygen which are chemically combined in such a manner as to form a definite and discrete inorganic chemical compound generally referred to in the literature as magnesium chromite. This chromite, like many other chromites, is isostructural to the mineral spinel (magnesium aluminate) and consequently can be said to have the spinel structure which is a face-centered cubic form.

The catalysts of the present invention are predominately chromites, that is, they contain more than 50% by weight of the chromite. Preferably the catalysts contain 75% or more chromites, i.e., 90% chromites. The chromites generally may be represented by the formula $MeCr_2O_4$ where Me as stated above is Mg, however, a portion of the magnesium can be replaced with other metals having an ionic radius approximately between about 0.5 and 1.1Å, preferably between about 0.6 and 1.0Å. In the case of such mixed chromites, Mg will be the predominant Me ion, comprising at least 50 atomic % of the Me ions present. In addition to Mg the Me may be one or more of the divalent ions of Ca, Sr, Ba, Fe, Mn, Co, Ni, Cu, Zn, or Cd.

The magnesium chromites of the present invention exhibit a certain type of X-ray diffraction pattern. The peaks observed in the X-ray diffraction pattern may not have sharp peaks such as those found, e.g., in highly crystalline material of the same chemical composition, but can and do frequently exhibit relatively broad reflection peaks. The degree of sharpness of the reflection peak may be measured by the reflection peak band width at half height (W/h/2). In other words, the width of the reflection peak as measured at one-half of the distance to the top of the peak is the "band width at half height". The band width at half height is measured in units of °2 theta. Techniques for measuring the band widths are discussed, e.g., in Chapter 9 of Klug and Alexander, X-ray Diffraction Procedures, John Wiley and Son, N.Y., 1954. The observed band widths at half height of the preferred compositions of this invention are at least 0.12 °2 theta and normally will be at least 0.16 °2 theta.*

*The powder diffraction patterns may be made, e.g., with a Norelco constant potential diffraction unit type No. 12215/0, equipped with a wide range goniometer type No. 42273/0, copper tube type No. 32147, proportional counter type No. 57250/1; all coupled to the Norelco circuit panel type No. 12206/53. The copper K alpha radiation is supplied by operating the tube at a constant potential of 40 kilovolts and a current of 35 milliamperes. A nickel filter is used to remove K beta radiation. The detector voltage is 1600 volts and the pulse height analyzer is set to accept pulses with amplitudes between 10 and 30 volts only. Slits used are divergence 1°, receiving 0.006 inches and scatter 1°. Strip chart recordings for identification are made with a scanning speed of 1° per minute, time constant of 1 second and a full scale at $10^3$ counts per second. No correction is made for Kα doublet or instrumental broadening of the band widths.

The particular reflection peak used to measure the band width at one-half height is the reflection peak having Miller (hkl) indices of 111. (See, e.g., Chapter of Klug and Alexander, ibid). This description is not to be taken as a limitation of the invention in regard to the relationship between composition activity and band width.

Suitable catalyst according to this invention is magnesium chromite having X-ray diffraction peaks with the d-spacings 4.80–4.82, 2.94–2.96, 2.50–2.52, 2.40–2.42, 2.07–2.09, 1.90–1.92, 1.69–1.71, 1.59–1.61, 1.46–1.48, 1.40–1.42, and the most intense peaks being between 2.50–2.52.

Chromite formation can be accomplished by reacting an active compound of chromium with an active compound of magnesium and the other designated metals. By active compound is meant a compound which is reactive under the conditions to form the chromite. Starting compounds of chromium, magnesium or the other metals may be such as the nitrates, hydroxides, hydrates, oxalates, carbonates, acetates, formates, halides, oxides, etc.

The catalyst may contain an excess of chromium over the stoichiometric amount, which is 2 atoms of chromium per atom of Me ($MeCr_2O_4$). There may be from 10 to 200 percent excess of the chromium. Similarly the Me portion of the chromite may be present in more than a stoichiometric amount.

The magnesium chromite can be prepared by precipitation, dry or wet milling or mixing, by precipitation of one of the ingredients in the presence of the other, coprecipitation and impregnation of one or more of the solid ingredients with aqueous or non-aqueous solutions of salts of the ingredients.

The present invention has been found to be particularly beneficial when the magnesium chromite has been prepared by intimate mixing of the solid components, such as by a slurrying procedure.

It has now been discovered that improved magnesium chromites for use as dehydrogenation catalysts are obtained by the inclusion of an alkali metal as part of the catalysts. This is conveniently achieved by adding the alkali metal component as a soluble or insoluble compound in a slurry of magnesium chromite or magnesium chromite precursors. When employed as an insoluble compound, the alkali metal will be in a finely divided state, i.e., a powder.

The alkali metals of particular interest are Li, Na, K, Rb and Cs, with Li, Na and K forming a particularly preferred group. Generally up to about 10 mol percent based on the weight of magnesium chromite of the alkali metal may be employed. The magnitude of the modifying effect of the alkali metal on the magnesium chromite will vary from metal to metal and the 10 mol percent represent an upper limit with the one of the lesser active of these, e.g., Li. Sodium appears to be the most active of the modifiers and would be used in lesser amounts than the Li. Other factors such as the method of catalyst preparation, i.e., calcination temperature, calcination atmosphere, other catalysts modifiers and the like will also effect the optimum amount of alkali modifier to be employed within the range of about 0.5 to 10 mol percent.

A particularly useful alkali metal is Li which is moderate in its actions on the present chromite and amounts of from about 1.0 to 10 mol percent thereof can be beneficially employed with about 2.0 to 8.0 mol percent being a preferred range.

A particularly preferred magnesium chromite is one such as described and claimed by the present inventor in U.S. Pat. No. 3,781,376 wherein the magnesium chromite contains aluminum therein; and the disclosure of that patent in regard thereto is incorporated herein. The preferred catalyst contains chromium, magnesium, aluminum and oxygen. The catalysts are characterized as magnesium chromites either in admixture with aluminum oxide or containing aluminum therein and can be considered as aluminum promoted magnesium chromites.

The aluminum component of the catalyst may also be present as a constituent of the chromite, however, it is not necessary that the aluminum be a portion of the chromite and may be present in addition to the metal chromite in the form of aluminum oxide. The aluminum can be incorporated into the chromite by backing out a portion of the chromium. Aluminum can be substituted for up to less than 50% of the chromium atoms of the chromite. Such chromites have the formula $MeAl_xCr_{2-x}O_4$ where Me has the designation previously given and x is a number of from more than 0 up to less than 1.

The aluminum component of the catalyst can be added prior to and/or after the calcination and formation of the chromite. The aluminum component is conveniently added to the chromite as a soluble salt in a slurry with the chromite after which it is dried; then decomposed by heating to aluminum oxide. Alternatively insoluble aluminum oxide can be added to the magnesium chromite, preferably in a highly divided state. Yet another desirable way to place the aluminum in the catalyst is by coprecipitation of aluminum hydroxide with the Me hydroxide and chromium hydroxide.

The aluminum will be present in the catalyst in all forms in an atomic ratio of Al:Cr of 0.0004 to 1.2:1. For example, in terms of a soluble aluminum compound such as aluminum sulfate, added to the magnesium chromite this would represent from about 0.1 to 75 weight percent $Al_2(SO_4)_3.16H_2O$ based on the total weight of the catalyst. A preferred range of Al:Cr atom ratio is 0.04 to 0.8:1. Generally the higher weight percentages of aluminum compound, i.e., 50 weight percent or more, are applied to the magnesium chromites having high surface areas, e.g., $50m^2$ per gram or more.

The active catalysts can be pelleted or applied to a suitable support, such as alumina, silica gel, silica-alumina, firebrick, kieselguhr, quartz and the like. The catalyst is the active surface available for contact with the gaseous reactants.

The formation of the chromite is obtained by heating the slurry or other intimate mixture of chromite precursors at an elevated temperature, e.g., 400°–1100° C. (generally no greater than 1300° C.), in a controlled atmosphere, as described below, i.e., usually 5 minutes to 4 hours. A calcination temperature of 550°–900° C. has been found particularly useful and temperature in the range of 600°–800° C. have been found to produce excellent catalysts.

The formation of the chromite is obtained by heating the precipitates or other intimate mixture of chromite precursors at an elevated temperature, in a controlled atmosphere, i.e., air, nitrogen, helium, a reducing atmosphere such as hydrogen, carbon monoxide or the like, for a sufficient time, i.e., usually 5 minutes to 4 hours.

Particularly preferred magnesium chromite is formed in an atmosphere containing less oxygen than normally contained in air, such as less than 15 or 20 mol percent oxygen. By thus causing the reaction to take place in an atmosphere deficient in oxygen, the metal portion of the chromite is less prone to be oxidized to a higher valence. The reaction to form the chromite is preferably essential in the absence of oxygen, preferably a non oxidizing atmosphere, such as in an atmosphere of nitrogen or helium. The nature of a preferred atmosphere used to calcine or sinter the metal chromite precursors is one in which the reactants and the metal chromites produced are essentially inert. Thus the atmosphere would be an essentially inert atmosphere rather than either an essentially oxidizing atmosphere or an essentially reducing atmosphere, although small quantities of non-inert gases, e.g., either or both of oxidizing or reducing gases, or other reactive gases, i.e., about up to 3 mol percent would be acceptable in the preferred embodiment. As defined herein an inert atmosphere comprises essentially nitrogen, helium, neon, argon, krypton, xenon, radon, and mixtures thereof.

Halogen may be present during the magnesium chromite formation. The exact function of the halogen is not fully understood. Apparently, the halogen catalyzes the solid state reaction of the precursor ingredients to form the magnesium chromite product.

The halogen may be present in any suitable form wherein the halogen can be in intimate contact with the reactants during chromite formation. The halogen may be present in the reaction atmosphere as molecular halogen or as volatile halogen compounds such as HX or $NH_4X$. However, a preferred method is to introduce the halogen by way of a solid inorganic compound which at least partially decomposes during chromite formation. Chromium or magnesiumhalides(or hydrates thereof) are entirely satisfactory and desirable. Generally the halogen will be chlorine, bromine or iodine with chlorine being the preferred halogen. Suitable sources of halogen are such aS $Cl_2$, $Br_2$, $I_2$, HCl, HBr, HI, $NH_4Cl$, alkyl halides containing 1 to 6 carbon atoms such as methyl chloride, halohydrins such as ethylene chlorhydrin, halosubstituted aliphatic acids such as chloro-acetic acid, organic amine halide salts of the general formula $R_3N.HX$ wherein R is a hydrocarbon radical containing from 1 to 8 carbon atoms such as methyl amine hydrochloride or hydrobromide and other halogen compounds such as $CrBr_3$, $CrCl_3$, $CrF_3$, $MgCl_2$, $MgBr_2$, $CCl_4$ and the like; or $MnCl_2.4H_2O$, $MnI_2$, $FeCl_3.6H_2O$, $FeF_2$ or the like where a portion of the Mg is to be replaced in the chromite.

Generally, halide compounds will be used which require a temperature of no greater than 450° C. to exert a vapor pressure of at least 1 mm of Hg at atmospheric pressure. Data showing the temperature necessary to achieve 1 mm of Hg vapor pressure of various metal halides may be found on page 650 of Industrial and Engineering Chemistry, Vol. 39, No. 4, Apr. 1947, which article is incorporated herein by reference. However, halogen compounds other than those listed in that reference are useful according to this invention. Ordinarily, the halogen compound will have from 0 to 8 carbon atoms and will have a molecular weight of less than 750. As mentioned, the function of the halogen is not fully understood. Furthermore, the actual mechanism during the reaction is also not fully understood. However, it is generally thought to be desirable to have the halogen present in an amount of from 0.0001 to 1.0 mols of halogen (calculated as mols of halogen, $X_2$) per atom of chromium present in the chromite reactants. This halogen may be present either in the solid phase, volatile phase or combinations thereof. Generally speaking, the vapor atmosphere present during chromite formation (which is considered at the temperature at which chromite can first be detected and usually will be at a temperature of at least 250° C. to 350° C.) will contain from 0.0001 to 3 mol percent of halogen (calculated as mols percent of $X_2$), and preferably from 0.01 to 1 mol percent of the atmosphere. These ratios may be varied somewhat depending upon reaction conditions, and other considerations as stated herein.

In a particular embodiment of the present invention water insoluble or essentially insoluble precursors of magnesium chromite such as, for example, fine powders of $MgCO_3$, $MgCO_3Mg(OH)_2.3H_2O$, $MgF_2$, MgO, $MgSiO_3$, CrO, CrB, $Cr_3C_2$, CrN, $CrO_2$, $Cr_2O_3$, $Cr_2O_3.XH_2O$, $2Cr_2O_3.CrO_3.XH_2O$ and the like are slurried to form an intimate mixture of the components (including halogen components if any). This mixture is then dried, preferably at temperatures below about 150° C. or at about 100°–135° C. The dried material is then calcined as indicated above. The calcined material will contain magnesium chromite, as has been established by X-ray diffraction analysis. This material in this embodiment is then mixed in a slurry with an aluminum component, deposited on a support and dried.

The catalysts of this invention can be applied to the dehydrogenation of a wide variety of organic compounds, particularly parafin and olefin hydrocarbon compounds. Such compounds normally will contain from 2 to 20 carbon atoms, at least

grouping, having a boiling point below about 350° C., and may contain other elements, in addition to carbon and hydrogen such as oxygen, halogens, nitrogen and sulfur. Preferred are compounds having 2 to 12 carbon atoms, and especially preferred are compounds of 3 to 8 carbon atoms.

Representative materials which are dehydrogenated by the novel process of this invention include n-butane, ethyl toluene, alkyl chlorobenzenes, ethyl naphthalene, isobutyronitrile, propyl chloride, isobutyl chloride, ethyl fluoride, ethyl bromide, n-pentyl iodide, ethyl dichloride, 1,3-dichlorobutane, 1,4 dichlorobutane, the chlorofluoroethanes, methyl pentane methylethyl ketone, diethyl ketone, n-butyl alcohol, methyl propionate, isobutane, ethylbenzene and the like.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, cycloalkanes, alkanes, alkenes and the like.

Suitable dehydrogenation reactions are the following: acyclic compounds having 4 to 5 non-quarternary contiguous carbon atoms to the corresponding olefins, diolefins or acetylenes having the same number of carbon atoms; aliphatic hydrocarbons having 6 to 16 carbon atoms and at least one quaternary carbon atom to aromatic compounds, such as 2,4,4-trimethylpentene-1 to a mixture of xylenes; acyclic compounds having 6 to 16 carbon atoms and no quaternary carbon atoms to aromatic compounds such as n-hexanes to benzene; cycloparaffins and cycloolefins having 5 to 8 carbon atoms to the corresponding olefin, diolefin or aromatic compound, e.g., cyclohexane to cyclohexene or cyclohexadiene or benzene; aromatic compounds having 8 to 12 carbon atoms including one or two alkyl side chains of 2 to 3 carbon atoms to the corresponding aromatic with unsaturated side chain such as ethyl benzene to styrene.

Illustration of dehydrogenations include butane to butenes and butadiene; propionitrile to acrylonitrile; propionaldehyde to acrolein; ethyl chloride to vinyl chloride; methyl isobutyrate to methyl methacylate; 2 or 3-chlorobutene-1 or 2,3-dichlorobutane to chloroprene; ethyl pyridine to vinyl pyridine; ethylbenzene to styrene; isopropylbenzene to α-methyl styrene; ethylchlorohexane to styrene; cyclohexane to benzene; ethane to ethylene to acetylene; propane to propylene or methyl acetylene or allene; isobutane to isobutylene; isopentane to isoanylene and isoprene; n-butene to butadiene-1,3 and vinyl acetylene; methyl butene to isoprene; cyclopentane to cyclopentene and cyclopentadiene; n-octane to ethyl benzene and orthoxylene; monomethylheptanes to xylenes; ethyl acetate to vinyl acetate; 2,4,4-trimethylpentane to xylenes; and the like.

The preferred compounds to be dehydrogenated are hydrocarbons with a particularly preferred class being acyclic non-quaternary hydrocarbons having 3 to 5 carbon atoms or ethyl benzene and the preferred products are propene, n-butene-1 or 2, butadiene-1,3vinyl acetylene, 2-methyl-1-butene, 3-methyl-1-butene, 3-methyl-2-butene, isoprene, styrene or mixtures thereof. Especially preferred as feed are n-butane, isopentane, ethyl benzene mixtures thereof such as hydrocarbon mixtures containing these compounds in at least 50 mol percent.

The dehydrogenation reaction may be carried out at atmospheric pressure, superatmospheric pressure or at sub-atmospheric pressure. The total pressure of the system will normally be about atmospheric pressure or sub-atmospheric pressure. Generally the total pressure will be between about 1 p.s.i.a. and about 75 p.s.i.a. Preferably the total pressure will be less than about 50 p.s.i.a.

The temperature of the dehydrogenation reaction will generally be in a range of about 350° to 700° C. with excellent results being obtained in the range of 400° to 650° C. The gaseous reactants can be conducted through the reaction chamber at a fairly wide range of flow rates. The optimum flow rates will be dependent upon such variables as the temperature of reaction, pressure, particle size of the catalyst, and so forth. Desirable flow rates may be established by one skilled in the art. Generally the flow rates will be within the range of about 0.10 to 10 liquid volumes of the organic compound to be dehydrogenated per volume of dehydrogenation zone containing catalyst per hour (referred to as LHSV). Usually the LHSV will be between 0.15 and about 5. For calculation, the volume of a fixed bed dehydrogenation zone containing the catalyst is that original void volume of reactor space containing catalyst.

The dehydrogenation is carried out in a series of cycles which comprise dehydrogenation of a suitable feed over the catalysts of the invention under the conditions as defined for a period of time, usually about 6 to 12 minutes followed by a regeneration cycle during which the coke deposited from the dehydrogenation is burnt off. The regeneration can be longer or shorter than the dehydrogenation cycle as needed to remove the coke, usually about 6 to 12 minutes will be sufficient. The coke is removed by passing oxygen at a temperature of 550° to 650° C. over the catalyst. A convenient source of oxygen is air, however, pure oxygen or a mixture of oxygen with inert gases, such as nitrogen, either in the same or different proportions as air, can be used.

The following Examples which are submitted to demonstrate the operation of the invention are divided into two sections relative to the reactor. In the first section, the dehydrogenation process was carried out at atmospheric pressure, i.e., about 15 p.s.i.a. In the second section, a vacuum reactor was employed. The absolute numbers of the results may vary as compared between the atmospheric and vacuum reactors, however, the trends, results and relative differences in catalyst types are comparable. The presence of the chromite structure was established for the catalysts by X-ray analysis as described previously. In the Examples, percents are by weight except that results are given as mol percents. Analysis of the products was by gas-liquid chromatography. The alkali is described as a mol percent in some examples. This means $$\frac{\text{mols of Alkali component}}{\text{mols of } MgCr_2O_4} \times 100.$$

Isothermal Atmospheric Reactor (Examples 1-14)

The reactor was a 29×¾ inch Vycor tube equipped with a heating mantle and appropriate equipment. A 40 cc bed of catalyst was placed in the reactor and reactant feed (or regenerative air) passed over it. The catalyst was heated to the reaction temperature in a nitrogen atmosphere. The process was carried out automatically with a make cycle (dehydrogenation) of 9 minutes and 9 minutes oxygen regeneration and repeat of the cycle. This gave a total cycle time of 18 minutes. When desired, the partial pressure of the n-butane during the reaction cycle was reduced below atmospheric by dilution with nitrogen. The total effluent from either or both cycles was collected in an inflatable collecting device and analyzed by gas chromatography. Alternately, the effluent from the regeneration cycle was passed through a calibrated infrared analyzer to determine the amount of $CO_2$ produced during regeneration (coke burn-off). By either method of analysis the amount of coke deposited on a catalyst during the reaction cycle was determined and could be taken into account when calculating the overall activity and selectivity of a catalyst. The temperatures were controlled by a thermoelectric temperature controller and recorded on a Leeds and Northrup 24-hour recorder.

EXAMPLES 1-3

Magnesium chromite was prepared by slurrying 62.3g basic magnesium carbonate (Merck Marinco CL, 43% MgO), 7.1g $MgCl_2.6H_2O$ (Baker Analyzed Reagent lot 36664, 99.8%) and 155.8g hydrated $Cr_2O_3$ (68.3% $Cr_2O_3$) with about 450ml deionized water. The slurry was dried overnight at 120° C., screened to sub 40 mesh particles, calcined to 800° C. in $N_2$, modified with 30 wt % $Al_2(SO_4)_3.16H_2O$ (Baker Analyzed Reagent lot 41022, 99.4%) and supported as 50% actives on 7-9 mesh AMC. A similarly prepared catalyst was made up with 2.5 mol % $Li_2CO_3$ (Baker Analyzed Reagent lot 29390-99.2%) added when the slurry was prepared. Isopentane was pumped at a liquid hourly space velocity of 1. The isopentane was vaporized and diluted with nitrogen to give an isopentane partial pressure of ⅓ atmosphere. A commercial dehydrogenation catalyst was run for comparison.

The isopentane and $N_2$ was carried down over the catalyst bed which was heated to 500°-600° C. It was found that the presence of Li reduced isomenzation of the feed. The results given in tabular form below (TABLE 1).

TABLE I

| EXAMPLE | | Temp. °C. | RESULTS | | | | | Mol % | | | |
|---|---|---|---|---|---|---|---|---|---|---|---|
| | | | C | S | | | | Y | | | |
| | | | | Am | iso | pen | Pip | Am | Iso | Pen | Pip |
| 1 | (No Alkali) | 535 | 55.9 | 73.4 | 10.5 | 6.2 | 3.3 | 40.9 | 5.8 | 3.6 | 1.9 |
| 2 | (2.5 mol % LiCO₃) | 555 | 49.0 | 72.8 | 12.2 | 1.7 | 0.2 | 35.7 | 6.0 | 0.8 | 0.1 |
| 3 | Cr0211T* | 550 | 52.6 | 53.6 | 8.0 | 9.9 | 4.0 | 28.2 | 4.2 | 4.7 | 2.1 |

Am = Isoamylenes;
Iso = Isoprene; Pen = n-pentylenes; Pip = piperylenes
*Commercial dehydrogenation catalyst. The Harshaw Chemical Company, Cleveland, Ohio.

EXAMPLES 4–7

These examples demonstrate the effect of calcination temperature on and alkali (Li) source on the effectiveness of the catalyst. The catalysts were prepared as those of Example 2 with the variation being indicated in the TABLE II below, along with the results of butane dehydrogenation. Substantially the same reaction conditions were maintained for each run.

TABLE II

| EXAMPLE | | C | $S_{Bu}$ | $S_{Rd}$ | $Y_{Bu}$ | $Y_{Bd}$ |
|---|---|---|---|---|---|---|
| 4 | 0.5 mole % Li₂O from carbonate | 66.0 | 73.0 | 11.8 | 48.1 | 7.2 |
| 5 | 2.5 mole % Li₂O from carbonate | 64.8 | 72.3 | 16.6 | 46.9 | 10.8 |
| 6 | 2.5 mole % Li₂O from chloride | | | | | |
| | calcined 650° C. | 56.2 | 72.4 | 12.8 | 40.7 | 7.2 |
| | calcined 700° C. | 61.9 | 71.9 | 12.4 | 44.4 | 7.7 |
| | calcined 750° C. | 63.0 | 73.3 | 11.7 | 46.2 | 7.0 |
| | calcined 800° C. | 64.8 | 73.6 | 12.1 | 47.7 | 7.8 |
| 7 | 2.5 mole % Li₂O from carbonate | | | | | |
| | calcined 650° C. | 62.5 | 70.5 | 15.8 | 44.0 | 9.8 |
| | calcined 700° C. | 64.6 | 70.9 | 15.6 | 45.8 | 10.1 |
| | calcined 750° C. | 66.0 | 71.1 | 15.2 | 46.9 | 10.1 |
| | calcined 800° C. | 66.7 | 71.1 | 15.3 | 47.4 | 10.2 |

EXAMPLES 8–14

In this group of examples the procedures as described for the catalyst of Example 2 was followed, but various amounts of Li were employed and different amounts of Al as Al₂(SO₄)₃.16H₂O. The conditions and results are in Table III.

TABLE III

| Experiment Conditions | LHSV = 1.0, $T_m$ = ~600° C. Reaction Cycle = 9 minutes reaction/9 minutes regeneration; pp of the hydrocarbon feed (hcbn + N₂ diluent) = 0.33 atm. |
|---|---|
| Hydrocarbon Feed: | 99 Mol % minimum n-butane |
| Catalyst: | MgCr₂O₄ coataining X mole % Li (Li₂CO₃) + Al₂(SO₄)₃ · 16 H₂O deposited on 7–9 mesh AMC. |

| Ex. | Mole % Li | Wt. % Al₂(SO₄)₃· 16 H₂O in actives | Results[1] | | | | |
|---|---|---|---|---|---|---|---|
| | | | C | $S_{Bu}$ | $S_{Bd}$ | $Y_{Bu}$ | $Y_{Bd}$ |
| 8 | 0 | 25 | 65.5 | 64.8 | 14.6 | 42.4 | 9.5 |
| | | 30 | 67.3 | 66.5 | 15.2 | 44.7 | 10.2 |
| | | 35 | 65.9 | 69.3 | 14.6 | 45.7 | 9.6 |
| | | 40 | 65.5 | 69.3 | 13.7 | 45.4 | 9.0 |
| 9 | 3 | 25 | 66.7 | 60.3 | 15.9 | 40.2 | 10.6 |
| | | 30 | 72.3 | 67.3 | 14.6 | 48.7 | 10.5 |
| | | 35 | 71.2 | 69.4 | 14.2 | 49.4 | 10.1 |
| | | 40 | 66.0 | 70.8 | 14.4 | 46.7 | 9.5 |
| 10 | 4 | 25 | 67.0 | 69.9 | 14.0 | 46.9 | 9.4 |
| | | 30 | 71.7 | 67.0 | 16.0 | 48.0 | 11.5 |
| | | 35 | 73.3 | 67.7 | 14.9 | 49.6 | 10.9 |
| | | 40 | 69.7 | 71.6 | 13.8 | 49.9 | 9.6 |
| 11 | 6 | 30 | 65.3 | 71.6 | 11.8 | 46.8 | 7.7 |
| | | 35 | 69.4 | 71.3 | 13.7 | 49.4 | 9.5 |
| | | 40 | 71.4 | 71.5 | 13.2 | 51.0 | 9.4 |
| | | 45 | 64.0 | 71.6 | 14.6 | 45.9 | 9.3 |
| 12 | 8 | 30 | 51.0 | 63.4 | 16.3 | 32.3 | 8.3 |
| | | 35 | 58.1 | 69.3 | 15.8 | 40.2 | 9.2 |
| | | 40 | 63.5 | 68.5 | 16.2 | 43.5 | 10.3 |
| | | 45 | 63.2 | 72.0 | 16.0 | 45.5 | 10.1 |
| 13 | 10 | 30 | 44.8 | 62.9 | 12.5 | 28.2 | 5.6 |
| | | 35 | 48.5 | 68.4 | 14.3 | 33.2 | 6.9 |
| | | 40 | 56.0 | 68.7 | 14.9 | 38.5 | 8.4 |
| | | 45 | 63.3 | 72.4 | 14.6 | 45.8 | 9.2 |
| 14 | 8[2] | 35 | 58.4 | 64.9 | 15.3 | 37.9 | 9.0 |
| | | 40 | 66.0 | 67.5 | 15.6 | 44.5 | 10.3 |
| | | 45 | 68.9 | 68.6 | 15.8 | 47.3 | 10.7 |

TABLE III-continued

| | Experiment Conditions | LHSV = 1.0, $T_m = \sim 600°$ C. Reaction Cycle = 9 minutes reaction/9 minutes regeneration; pp of the hydrocarbon feed (hcbn + $N_2$ diluent) = 0.33 atm. |
|---|---|---|
| | Hydrocarbon Feed: | 99 Mol % minimum n-butane |
| | Catalyst: | $MgCr_2O_4$ coataining × mole % Li ($Li_2CO_3$) + $Al_2(SO_4)_3 \cdot 16\ H_2O$ deposited on 7-9 mesh AMC. |

| Ex. | Mole % Li | Wt. % $Al_2(SO_4)_3 \cdot 16\ H_2O$ in actives | C | $S_{Bu}$ | $S_{Bd}$ | $Y_{Bu}$ | $Y_{Bd}$ |
|---|---|---|---|---|---|---|---|
| | | 50 | 67.4 | 68.6 | 15.7 | 46.2 | 10.6 |

(1)After ~24 hours on stream.
(2)Calcination temperature of the chromite preparation was 700° C. rather than the usual 800° C. for other preparations.

Isothermal Vacuum Reactor (Examples 15-17)

The reactor was an alonized 316 SS tube, 24 inches long and 1 inch in diameter equipped with a heating mantel and thermoelelectric temperature controller. A 160 cc bed of catalyst (112 cc of catalyst mixed with 48 cc of fused alumina balls) was used for each run. The reactant feed was passed down through the catalyst bed and the products removed at the bottom. The catalyst was heated to reaction temperature in a nitrogen atmosphere. The process was carried out in cycles of 9 minutes of reaction, 1 minute of nitrogen purge, 9 minutes of regeneration, followed by reaction, etc. A vacuum of 22 inches of Hg was maintained during the reaction cycle and atmospheric pressure used during nitrogen purge and regeneration cycle. Substantially the same analytical procedures were followed for the product gases as in the atmospheric process.

EXAMPLES 15 & 16

A magnesium chromite composition was prepared as in Example 2 except that 45 weight percent $Al_2(SO_4)_3 \cdot 16H_2O$ and 6 mol % Li was incorporated and the mixture tabletted with polyvinyl alcohol (combustible binder) into 5/32 inch diameter tablets. The conditions and results are set out in Table IV.

TABLE IV

Experimental Conditions: Pressure = 22" $H_2$ vacuum
Reaction Cycle: 9 min. reaction = 590 cc/min. of hcbn feed / 1 min. $N_2$ purge / 9 min. regeneration = 300 cc/min. $O_2$ + 1200 cc/min. $N_2$

| EXAMPLE | Catalyst | Total Hrs. on Stream | $T_m$, °C | Results, Mol % C/S + S /Y + Y Bu Bd Bu Bd |
|---|---|---|---|---|
| 15 | 5/32 " dia. tablets of $MgCr_2O_4$ + 6 mol % Li tabletted with 45 wt. % $Al_2(SO_4)_3 \cdot 16\ H_2O(+PVA)$. | 188(1) | 555 | 45.2/74.0+15.1/33.5+6.8 |
| | | 214 | 555 | 46.7/73.8+15.6/34.5+7.3 |
| | | 333 | 555 | 49.1/74.3+15.7/36.5+7.7 |
| | | 408 | 540 | 41.4/78.3+13.4/32.5+5.6 |
| | | 668 | 555 | 49.1/74.8+14.7/36.7+7.2 |
| | | 740 | 555 | 50.3/74.2+15.0/37.3+7.5 |
| | | 770(2) | 555 | 43.4/73.8+16.1/32.0+7.0 |
| | | 907 | 555 | 50.6/74.5+14.9/37.0+7.6 |
| 16 | CrO211 T; 5/32" dia. tablets | 296(1) | 550 | 47.4/76.3+12.6/36.2+6.0 |
| | | 349 | 550 | 45.5/77.7+11.2/35.4+5.1 |
| | | 470 | 550 | 43.2/77.7+12.4/33.6+5.4 |
| | | 517 | 550 | 42.0/77.8+2/32.7+5.5 |
| | | 729 | 550 | 40.2/76.5+14.0/30.8+5.7 |
| | | 803 | 550 | 38.4/77.3+14.5/29.6+5.6 |
| | | 851 | 570 | 50.2/70.7+16.9/35.6+8.5 |
| | | 902 | 570 | 50.2/70.4+17.1/35.3+8.6 |
| | | 971 | 570 | 48.9/71.4+17.0/35.9+8.3 |
| | | 1067 | 570 | 47.9/71.2+17.4/34.1+8.3 |
| | | 1139 | 570 | 46.8/71.6+17.3/33.6+8.1 |

(1)Feed = 90.2% n-butane + 7.3% butylenes + 2.3% isobutane
(2)Reaction cycle included a 0.3 min. reduction step with $H_2$ prior to the hydrocarbon dehydrogenation step.

It can be seen that the catalyst of the invention exhibited better time trends, higher selectivities at given conversions and higher conversions at given temperatures than the commercial dehydrogenation catalyst.

EXAMPLE 17

In this example, the feed was ethylbenzene. The catalyst was a magnesium chromite prepared as in Example 2 with 40 wt. %$Al_2(SO_4) \cdot 16H_2O$, 6 mol %Li pressed in 5/32" diameter pellets (PVA binder). The catalyst in the reactor was diluted 50/50 with inert alundum balls. The reactor was on stream 742 hours, and good results were observed along with an excellent time trend. The conditions and results are set out in Table VI.

TABLE VI

| Hrs. on Stream | Temp., °F. Start | End | LHSV | Vac. In. Hg. | C Ethylbenzene | S Styrene | Y Styrene |
|---|---|---|---|---|---|---|---|
| 27 | 961 | 946 | 1.0 | 27.5 | 20.7 | 93.1 | 19.3 |
| 51 | 1015 | 1003 | 1.0 | 27.5 | 37.6 | 94.8 | 35.7 |
| 70 | 1013 | 1001 | 1.0 | 28.0 | 56.3 | 91.9 | 51.8 |
| 167 | 1018 | 1001 | 1.0 | 28.0 | 63.7 | 90.3 | 57.5 |
| 215 | 1020 | 1001 | 1.0 | 27.5 | 60.1 | 89.7 | 54.0 |

TABLE VI-continued

| Hrs. on Stream | Temp., °F. Start | Temp., °F. End | LHSV | Vac. In. Hg. | C Ethylbenzene | S Styrene | Y Styrene |
|---|---|---|---|---|---|---|---|
| 239 | 1050 | 1030 | 1.0 | 27.5 | 65.1 | 89.4 | 58.2 |
| 263 | 1052 | 1032 | 1.0 | 27.5 | 65.3 | 90.3 | 59.0 |
| 360 | 1045 | 1025 | 1.0 | 27.5 | 64.7 | 91.3 | 59.0 |
| 431.5 | 1044 | 1025 | 1.0 | 27.5 | 63.0 | 92.2 | 58.1 |
| 437 | 1150 | 1072 | 2.0 | 27.5 | 58.6 | 93.3 | 54.6 |
| 512 | 1125 | 1071 | 2.0 | 27.5 | 56.6 | 94.3 | 53.3 |
| 526 | 1076 | 1057 | 1.0 | 27.5 | 66.8 | 90.9 | 60.7 |
| 550 | 1068 | 1049 | 1.0 | 27.0 | 65.6 | 92.5 | 60.7 |
| 574 | 1073 | 1051 | 1.0 | 27.5 | 66.2 | 91.6 | 60.6 |
| 581 | 1060 | 1050 | 1.0 | 27.5 | 66.6 | 91.7 | 61.1 |
| 719.5 | 1068 | 1049 | 1.0 | 27.5 | 65.5 | 92.4 | 60.5 |
| 725 | 1069 | 1052 | 1.0 | 27.5 | 65.7 | 92.9 | 61.0 |
| 742 | 1070 | 1051 | 1.0 | 27.5 | 65.4 | 92.7 | 60.6 |

The invention claimed is:

1. In the cyclic process for the dehydrogenation organic compounds comprising contacting a hydrocarbon having 3 to 8 carbon atoms and at least one

grouping with a catalyst to remove hydrogen from said organic compound and producing a compound having a higher degree of unsaturation than said hydrocarbon, terminating said dehydrogenation and regenerating said catalyst by contacting said catalyst uith molecular oxygen wherein the improvement comprises employing a dehydrogenation catalyst consistenting essentially of magnesium chromite having the general formula $MeCr_2O_4$ wherein Me is Mg or Mg and one or more of the divalent ions of Ca, Sr, Ba, Fe, Mn, Co, Ni, Cu, Zn or Cd, provided that Mg comprises at least 50 atomic percent of said Me ions and from 2 to 8 mol percent of Li based on said magnesium chromite.

2. The process according to claim 1 wherein Al is present as a promoter.

3. The process according to claim 1 wherein said hydrocarbon is acyclic non-quarternary having 3 to 5 carbon atoms or ethyl benzene.

4. The process according to claim 3 wherein said hydrocarbon comprises n-butane.

5. The process according to claim 3 wherein said hydrocarbon comprises isopentane.

6. The process according to claim 3 wherein said hydrocarbon is ethylbenzene.

* * * * *